(12) United States Patent
Guo

(10) Patent No.: US 8,084,923 B2
(45) Date of Patent: Dec. 27, 2011

(54) DIAGNOSTIC ULTRASOUND TRANSDUCER

(75) Inventor: Xiaocong Guo, Woodinville, WA (US)

(73) Assignee: MR Holdings (HK) Limited, Hong Kong (CN)

( * ) Notice: Subject to any disclaimer, the term of this patent is extended or adjusted under 35 U.S.C. 154(b) by 0 days.

(21) Appl. No.: 12/876,971

(22) Filed: Sep. 7, 2010

(65) Prior Publication Data

US 2010/0327698 A1    Dec. 30, 2010

Related U.S. Application Data

(63) Continuation of application No. 11/888,941, filed on Aug. 3, 2007, now Pat. No. 7,834,522.

(51) Int. Cl.
*H01L 41/08* (2006.01)
(52) U.S. Cl. ......... 310/334; 310/327
(58) Field of Classification Search ........ 310/334–336
See application file for complete search history.

(56) References Cited

U.S. PATENT DOCUMENTS

| | | | |
|---|---|---|---|
| 4,773,140 A * | 9/1988 | McAusland | 29/25.35 |
| 5,250,869 A * | 10/1993 | Ishikawa et al. | 310/334 |
| 5,296,777 A * | 3/1994 | Mine et al. | 310/334 |
| 5,559,388 A | 9/1996 | Lorraine et al. | |
| 5,567,657 A | 10/1996 | Wojnarowski et al. | |
| 5,617,865 A | 4/1997 | Palczewska et al. | |
| 5,703,400 A | 12/1997 | Wojnarowski et al. | |
| 5,722,137 A * | 3/1998 | Lorraine et al. | 29/25.35 |
| 5,810,009 A * | 9/1998 | Mine et al. | 600/459 |
| 5,920,972 A | 7/1999 | Palczewska et al. | |
| 5,923,115 A | 7/1999 | Mohr, III et al. | |
| 6,043,590 A * | 3/2000 | Gilmore | 310/367 |
| 6,541,896 B1 | 4/2003 | Piel, Jr. et al. | |
| 6,580,034 B2 | 6/2003 | Daane et al. | |
| 6,651,318 B2 | 11/2003 | Buck et al. | |
| 6,734,362 B2 | 5/2004 | Buck et al. | |
| 6,891,311 B2 * | 5/2005 | Phelps et al. | 310/317 |

(Continued)

FOREIGN PATENT DOCUMENTS

FR    2802449 A1    6/2001

OTHER PUBLICATIONS

Office Action dated Apr. 5, 2010 for U.S. Appl. No. 11/888,941.

(Continued)

*Primary Examiner* — Mark Budd
(74) *Attorney, Agent, or Firm* — Kory D. Christensen; Stoel Rives LLP

(57) ABSTRACT

An ultrasound transducer includes an array of PZT elements mounted on a non-recessed distal surface of a backing block. Between each element and the backing block is a conductive region formed as a portion of a metallic layer sputtered onto the distal surface. Traces on a longitudinally extending circuit board—preferably, a substantially rigid printed circuit board, which may be embedded within the block—connect the conductive region, and thus the PZT element, with any conventional external ultrasound imaging system. A substantially "T" or "inverted-L" shaped electrode is thereby formed for each element, with no need for soldering. At least one longitudinally extending metallic member mounted on a respective lateral surface of the backing block forms a heat sink and a common electrical ground. A thermally and electrically conductive layer, such as of foil, transfers heat from at least one matching layer mounted on the elements to the metallic member.

13 Claims, 5 Drawing Sheets

U.S. PATENT DOCUMENTS

| | | |
|---|---|---|
| 6,994,674 B2 | 2/2006 | Sheljaskow et al. |
| 7,229,292 B1 | 6/2007 | Haider et al. |
| 7,304,415 B2 | 12/2007 | Petersen et al. |
| 7,348,713 B2 | 3/2008 | Hashimoto |
| 7,834,522 B2 * | 11/2010 | Guo .............................. 310/335 |
| 2003/0085635 A1 | 5/2003 | Davidsen |
| 2006/0035481 A1 | 2/2006 | Petersen et al. |
| 2006/0186765 A1 | 8/2006 | Hashimoto |

OTHER PUBLICATIONS

Notice of Allowability dated Sep. 8, 2010 for U.S. Appl. No. 11/888,941.

* cited by examiner

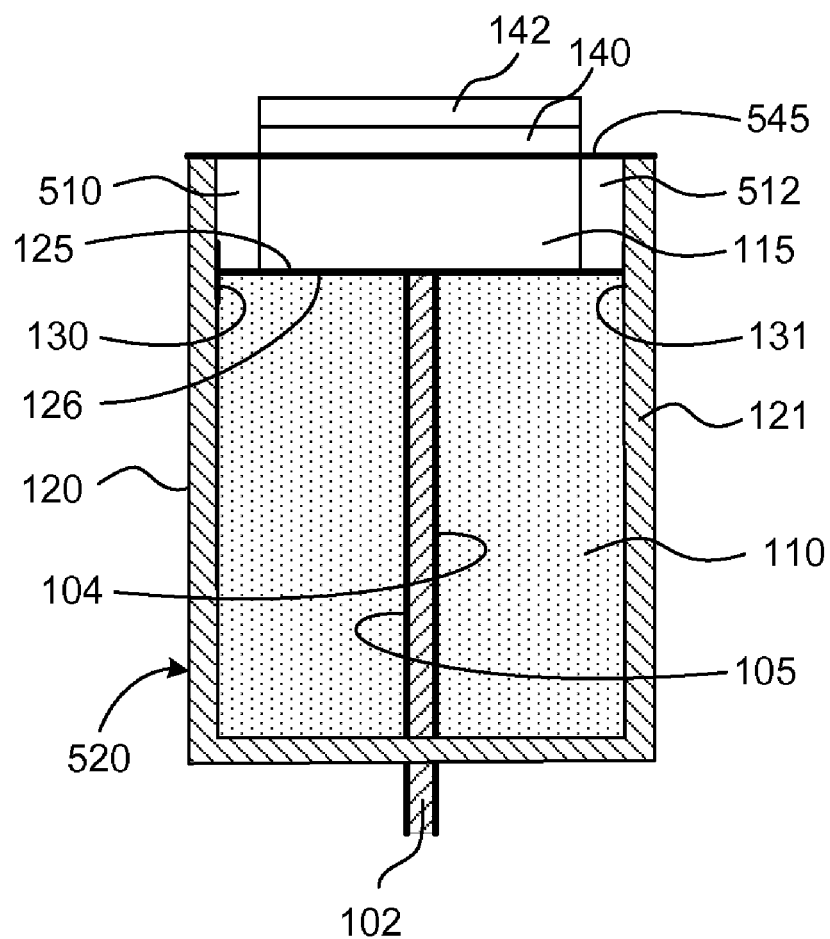

DIAGNOSTIC ULTRASOUND TRANSDUCER

BACKGROUND OF THE INVENTION

1. Field of the Invention

This invention relates to an ultrasonic transducer for use in diagnostic imaging.

2. Description of the Related Art

The importance of diagnostic ultrasound imaging is widely recognized, and has grown as imaging resolution and the range of available uses and features have steadily increased. Once an expensive luxury available only in the best-equipped hospitals, diagnostic ultrasound imaging is now a commonly and almost routinely offered procedure even in some individual physician's offices. Perhaps more importantly, some ultrasound imaging systems are now portable and inexpensive enough to have even in small offices, or in places such as in developing countries with relatively small budgets for such diagnostic tools.

The quality of an ultrasound image is directly affected by many factors and in particular by the properties of the transducer used to generate the necessary pattern of ultrasonic signals and to receive their echo returns. Accordingly, work is constantly in progress to improve almost every major component of a transducer, the materials used in it, and the methods of manufacturing it. During the past 30 years or so, just a few of the large number of improvements include better active materials, triple matching layers, better kerf filling, low-attenuation lens materials, heat treatments and heat sinks, and flex circuit interconnects.

Typically, piezoelectric elements within a transducer are formed as an array and are selectively activated electrically to produce a desired scan pattern. The same array is then switched to receive the return signals, which are then converted back into electrical signals that are processed using known methods. Individual and separate control of elements presumes, however, separate electrical leads in the form of wires, or traces on a circuit board, either printed (PCB) or flexible (flex circuit).

This reality leads to several challenges and trade-offs relating to such issues as, among many others, cross-talk, impedance, physical robustness, heat, integrity and ease of bonding, manufacturing cost and complexity, and even comfort in use. For example, strong lead wires may provide physical robustness, but they may also cause the transducer cable to be so bulky and stiff that it is cumbersome for an operator to maneuver over the body of a patient. However, fine wires or traces that allow for a light, flexible cable are more prone to breaking. As another example, certain transducer structures may be specially designed to be manufactured with certain materials, such as in a backing layer, but may then be difficult to adapt to new materials without difficult and costly changes in the structure and manufacturing procedures.

Many different transducer structures and cabling (including single, double, and multi-layer flex circuits) and interconnect arrangements have, accordingly, been proposed in different contexts involving diagnostic ultrasound imaging. The following U.S. patents, for example, represent proposed solutions to some of the many problems involved in different contexts of diagnostic ultrasound imaging transducers:

U.S. Pat. No. 5,559,388 (Lorraine, et al., "High density interconnect for an ultrasonic phased array and method for making");

U.S. Pat. No. 5,722,137 (Lorraine, et al., "Method for making a high density interconnect for an ultrasonic phased array");

U.S. Pat. No. 5,567,657 (Wojnarowski, et al., "Fabrication and structures of two-sided molded circuit modules with flexible interconnect layers");

U.S. Pat. No. 5,617,865 (Palczewska, et al., "Multi-dimensional ultrasonic array interconnect")

U.S. Pat. No. 5,920,972 (Palczewska, et al., "Interconnection method for a multilayer transducer array");

U.S. Pat. No. 6,994,674 (Sheljaskow, et al., "Multi-dimensional transducer arrays and method of manufacture");

U.S. Pat. No. 5,703,400 (Wojnarowski, et al., "Fabrication and structures of two-sided molded circuit modules with flexible interconnect layers");

U.S. Pat. No. 5,923,115 (Mohr, III, et al., "Low mass in the acoustic path flexible circuit interconnect and method of manufacture thereof");

U.S. Pat. No. 6,541,896 (Piel, Jr., et al., "Method for manufacturing combined acoustic backing and interconnect module for ultrasonic array");

U.S. Pat. No. 6,580,034 (Daane, et al., "Flexible interconnect cable with ribbonized ends");

U.S. Pat. No. 6,651,318 (Buck, et al., "Method of manufacturing flexible interconnect cable");

U.S. Pat. No. 6,734,362 (Buck, et al., "Flexible high-impedance interconnect cable having unshielded wires"); and U.S. Pat. No. 7,229,292 (Haider, et al., "Interconnect structure for transducer assembly").

There is nonetheless always room for improvement, not only in general, but also in the specific context of providing a transducer that is suitable for use beyond the well-controlled world of a diagnostic unit in a large-budget hospital. For example, a transducer for use in the field, or for wide-scale use in developing countries, should ideally be relatively easy to build and the component costs should be relatively low (to allow for greater numbers for a given budget); the performance should be as little limited or reduced as possible; it should be easy to adapt the transducer and its manufacturing process to take advantage of any newly developed materials, or to design changes such as in the number of matching layers. The transducer should also be physically robust and should preferably be more thermally tolerant than conventional probes. This invention at least partially meets one or more of these needs.

SUMMARY OF THE INVENTION

The invention relates to a diagnostic ultrasound transducer that has an array of electro-acoustic elements, such as PZT elements, mounted on a backing block. At least one matching layer is mounted on the array, as well as (for most implementations) a lens.

According to one aspect of some embodiments of the invention, the surface of the backing block on which the array is mounted is planar and non-recessed. For each electro-acoustic element in the array, an area of electrically conductive material is formed, for example by sputtering, on a corresponding portion of a contact surface of the backing block and in electrical contact with the electro-acoustic element.

In certain embodiments, a substantially rigid printed circuit board (PCB) is secured to or even within the backing block and extends in a longitudinal direction substantially perpendicular to the contact surface. For each electro-acoustic element, at least one electrically conductive trace is made on the circuit board in electrical contact with the corresponding contact surface portion and thereby with the electro-acoustic element. This creates a solder-free electrical signal path through the trace to the electro-acoustic element.

The circuit board may be either embedded within the backing block, which makes for easy mounting and secure positioning in a backing blocker used to mold the backing block, or mounted on a lateral surface of the backing block. Together with the traces and the conductive layer sputtered (for example) on the contact surface of the backing block, these embodiments provide a substantially "T" or "inverted-L"-shaped electrode for each element, with no need for soldering to provide good electrical contact.

At least one metallic member is preferably located on at least one side surface of the backing block, and extends longitudinally at least as far as the array. This member may be made as physically separate (but preferably electrically connected) plate- or sheet-like structures on either elevational side of the transducer, or as "arms" of a single frame- or box-like member that contacts the backing block on three sides. The metallic member may form a common electrical ground contact for the transducer. Where needed to prevent electrical shorting of the array elements' electrodes, an electrically insulating element may be mounted on the backing block to separate the metallic member from the electrically conductive material on the contact surface of the backing block.

At least one acoustic matching layer will normally be mounted on a transmitting surface of the array. An edge region of each metallic portion of each metallic member is preferably in direct or indirect thermal contact with a respective edge portion of at least one of the matching layers. For direct thermal contact, the metallic member extends longitudinally far enough to physically contact either side (elevational) or bottom edges of at least the innermost (closest to the backing block) matching layer. Indirect thermal contact may be provided using a thermally conductive, metallic layer, such as foil, located either between matching layers, or between at least the innermost acoustic matching layer and the array. The metallic member mounted on the sides of the backing block thereby may form not only a common electrical ground, but also a heat sink for heat flowing through the thermally conductive, metallic layer, as well as laterally from the electro-acoustic elements.

The invention also encompasses a method for making the transducer, which is especially advantageous for implementing embodiments of the invention in which the circuit board is a rigid PCB. The method includes: applying electrically conductive traces to at least one surface of the PCB; forming the backing block with the PCB secured to it; sputtering an electrically conductive layer onto the distal, non-recessed, planar contact surface of the backing block and a top edge of the PCB; mounting an electro-acoustic material on the contact surface of the backing block; mounting at least one matching layer on the electro-acoustic material; dicing the matching layer, the electro-acoustic material, and the electrically conductive layer into an array of electrically separated portions, each portion of the electro-acoustic material thereby forming a separate electro-acoustic element and each portion of the electrically conductive layer thereby forming an electrode connecting the electro-acoustic element to at least one of the traces; and, on at least one side of the backing block, mounting the metallic member (either the single "box-like" structure or electrically connected by physically separate elements such as plates) in contact with a lateral edge of the backing block and electrically insulated from the electrically conductive layer portion.

If "T" electrodes are to be made, then the PCB may be embedded in the backing block during the forming of the backing block. The rigidity of the PCB (as compared with, for example, a flex circuit), makes it much easier to ensure that the PCB location is fixed in the backing blocker (the structure that acts as a frame and mold for manufacturing the backing block), with less or no need for restraining or other supporting structures that also get embedded in the backing block and may cause image noise.

BRIEF DESCRIPTION OF THE DRAWINGS

FIG. 5 illustrates a metallic "box" that encloses much of a backing block and other structures of the probe.

DETAILED DESCRIPTION

Figure 1:
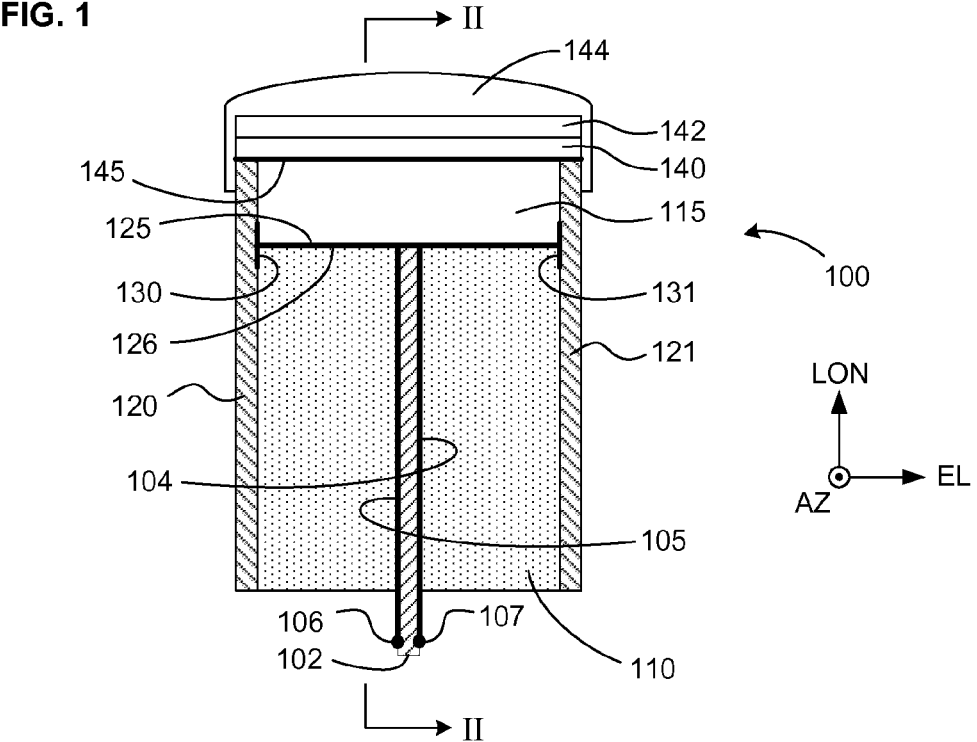
FIG. 1 shows a partially cut-away view from the side of the internal structure of one embodiment of an ultrasound probe according to the invention.
Figure 2:
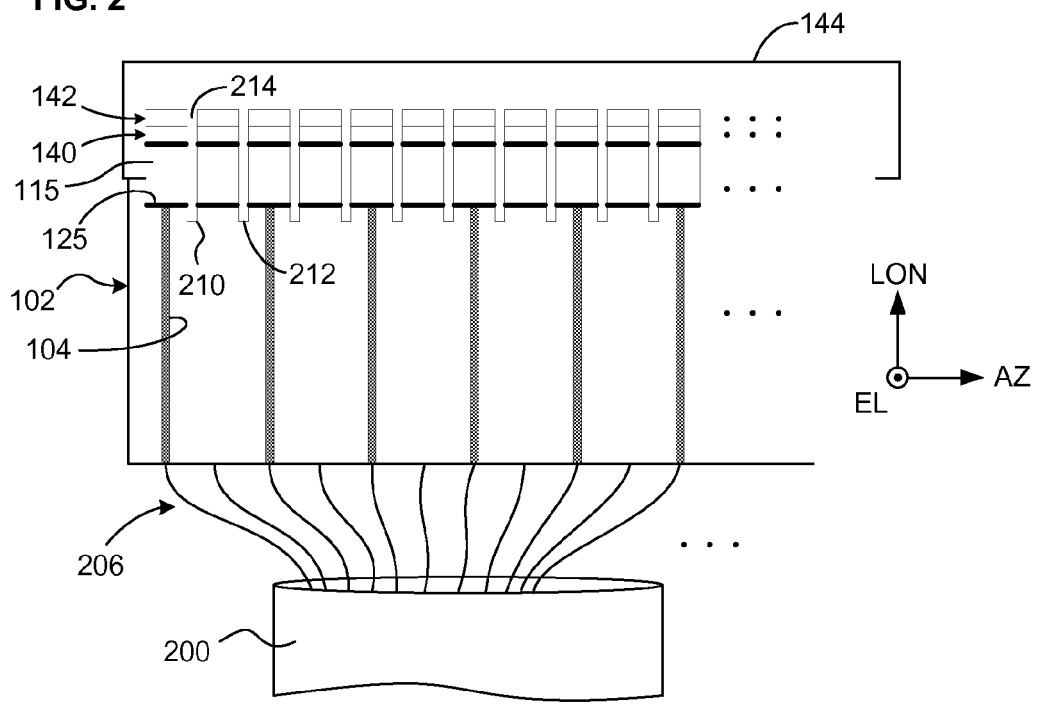
FIG. 2 is a partially cut-away view from the top of the transducer, taken along line II-II in FIG. 1.

FIG. 1 shows a partially cut-away view from the side of the internal structure of an ultrasound probe, that is, transducer 100 according to one embodiment of the invention. In FIGS. 1 and 2, coordinate systems indicating the conventional reference directions are indicated. Here, AZ, EL, and LON indicate the azimuthal, elevational, and longitudinal directions. The longitudinal direction, which is sometimes referred to as the axial direction, is the direction in which it is assumed that ultrasound energy will primarily radiate from each element of the transducer array. Viewed as in FIG. 1 and as the transducer is used in practice, the top of the transducer is the distal end and the bottom is the proximal end.

In particular, FIG. 1 shows one of typically many elements in an ultrasound transducer array—oriented as in FIG. 1, the array elements extend perpendicular to the plane of the figure, that is, in an azimuthal direction. Each element of the array will, in typical implementations, have the same essential structure as the one shown in FIG. 1. FIG. 2 shows a simplified cross-sectional view of the probe taken along line II-II of FIG. 1.

The invention may be used for probes with any chosen number of array elements consistent with the intended use for ultrasound imaging. Note that none of the figures is necessarily to scale—those skilled in the design of ultrasound transducers will choose the dimensions of the various features to meet the needs of each given implementation of the invention.

One or more outer and/or inner (for multi-layer) surfaces of a printed circuit board (PCB) 102 is provided in any known manner with one or more electrically conductive traces 104, 105 either as needed or desired for a given design choice. As is well known, traces for adjacent elements are often made on opposite sides of whatever substrate is used to carry them. This allows for a greater array density (element pitch) since traces for adjacent elements will not be too close together or too thin. Multilayer substrates allow for even greater density by providing for even more electrically separated surfaces to make traces on. The placement of traces is a design choice that transducer designers are well used to making. Note that, viewed as in FIG. 1, the PCB extends perpendicular to the plane of the figure.

In one prototype of the invention, the PCB 102 was a thin multilayer PCB. In general, the PCB is substantially rigid. Of course, no circuit board, PCB or otherwise, is completely rigid in the sense that it cannot be bent. In this description, "rigid" means that under normal operating conditions, neither the material nor the fabrication for the PCB 102 or the traces 104, 105 is chosen with the expectation that they will need to withstand any bending stress. By way of contrast, a flex circuit by this definition is not rigid.

The traces 104, 105 lead corresponding electrical signals from and to lead wires 106, 107, which are electrically connected with the main processing and control system (not shown) of the ultrasonic imaging device in any known manner. In FIG. 2, the wires are shown collectively as 206 entering a standard ribbon cable 200, which will then lead signals between the probe and the main unit of the ultrasound imaging system. Other arrangements for connecting traces electrically with lead wires are known and may be used with any of the embodiments of this invention.

A backing block 110, which may be made of any conventional material such as epoxy mixed with some heavy, sound-absorbing material(s), forms the base of the probe. In the embodiment shown in FIG. 1, the PCB 102 is embedded in the backing block 110. In other words, the backing block 110 is molded around the PCB 102, for example, such that the PCB 102 extends substantially through the middle of the backing block 110 in the longitudinal direction.

This arrangement is not necessary, however, but rather the PCB 102 could instead be mounted on a side of the backing block 110, out of the acoustic path, which may be advantageous in high-frequency applications. The precise position of the PCB 102 can be determined by the chosen position of the blocking and mixing tool, and of the fixture of the lamination and dicing tool. The design and use of such tools and fixtures are well known in the field of transducer manufacture such that, after proper design and adjustment of the equipment, no special skills will be needed to manufacture the probe.

It would also be possible to include more than one PCB (each with its own traces) within or on the backing block 110, for example, in a 1.5- or higher-dimensional array. The structures and techniques described here may also be modified in ways apparent to those skilled in ultrasound transducer design to accommodate even non-linear array architectures.

An array 114 of electro-acoustic elements made, for example, of a suitable electro-ceramic material such as lead zirconate titanate (PZT) is mounted on the backing block 110 and is diced and filled in any conventional manner to form several elements, of which one—element PZT element 115— is shown in FIG. 1; it would also be possible to form the array as a series of individual electro-acoustic crystals. PZT elements formed by dicing a single block are, however, the most common such elements in ultrasound transducers and are assumed in this discussion for the sake of succinctness and clarity. Their properties, fabrication methods, proper dimensioning and operation are well-understood and are therefore not described in greater detail here.

Metallic members such as sheets or plates 120, 121, or a sufficiently thick deposit of some metallic material (here, "plate(s)" just for the sake of simplicity), may be bonded in any known way on either side of the backing block 100 and extend in contact with most and preferably all of the lateral edges (again, viewed as in FIG. 1) of the PZT elements of the array 115. These plates may be made of copper, aluminum, or any other metal that conducts heat well so as to form a thermal path for heat to flow away from the PZT element 115 and the backing block 110 to any external sink. The plates 120, 121, which are preferably electrically connected in known manner (including being portions of a single enclosing member—see below) also provide an effective common ground for various electrically conductive parts of the transducer and in particular for the PZT elements. If the PCB 102 is mounted on the side of the backing block 110, then the metallic plate 120, 121 on that side will either be mounted on the external surface of the PCB (assuming either that there are no traces on that side or that the traces are in some known way electrically isolated from the plate), or that plate may be omitted altogether.

A layer 125 of a conductive metal such as layered gold, or gold on nickel, is applied, for example deposited by sputtering, onto the top surface (thus, a contact surface) of the backing block backing block 110. In one prototype of the invention, the conductive layer 125 was a 3000 Å thick layer of sputtered gold, which is relatively easy to do compared with what is typically required for element contact in prior art probes. Preferably, the entire top surface of the backing block 110 is provided with the conductive layer 125 so as to provide the best electrical contact with the PZT element 115. To ensure good electrical contact, the bottom surface of the PZT element 115 may also be provided with a similar sputtered-on conductive layer 126, although this will in many cases be an optional feature. The upper surface of the backing block 110 is preferably prepared by being smoothed and polished so as to have as flat an upper surface as possible, thus providing full surface contact between the layer 125 and the underside of the element 115.

The traces 104, 105 extend up to and join with the conductive layer 125, thereby forming an uninterrupted electrical path to each PZT element with no need for soldering. In essence, a solder-free, "T-shaped" electrode (the traces 104, 105 on the PCB 102 and the layer 125) is provided, with full electrical contact with the underside of PZT element. Of course, if the PCB is mounted on the side of the backing block 110 and is not embedded, then the electrode will have the shape of an inverted "L". Although in theory (and often in practice) only one trace will be needed per PZT element to provide electrical contact, more than one trace per element may be provided to increase the likelihood and integrity of electrical contact with the conductive layer 125 and thus with the PZT element.

As FIG. 2 illustrates, dicing cuts 210, 212 (only two are labeled, for simplicity), extend all the way through the matching layer(s), the PZT layer and the conductive layer 125 into the backing block so as to isolate the PZT elements electrically from each other, in particular, so that the metallic layer 125 will not electrically short any of the elements. One should keep in mind that the figures are not necessarily to scale—in most actual probes made according to any embodiment, there may be well over 100 (and in some cases several hundred) PZT elements in a linear array, and even more in a 2-D array. Merely for the sake of clarity, the figures do not attempt (or, for those skilled in transducer design and manufacture, need) to show the sizes of the elements 115 in the figures relative to the actual dimensions of, for example, the width of a typical lens 144 or the length of typical traces. Moreover, FIG. 2 also illustrates how traces for, for example, adjacent PZT elements may be located on opposite sides of the PCB 102, such that only traces 104 are visible in FIG. 2.

The conductive layer 125 is preferably electrically insulated from the metallic plates 120, 121, for example by strips 130, 131 of a non-conductive material such as Kapton/polyimide bonded to the sides of the backing block 110 and the PZT element 115 where these meet. Viewed as in FIG. 1, these strips would extend perpendicular to the plane of the figure, in the azimuthal direction, along the width of the array 114 (on both or only one side, depending on the mounting of the PCB) where the array meets the block 110. Although more complicated (attaching the strips 130, 131 is easy to do and the strips themselves are easy to make), it would also be possible to omit a small region of the conductive layer 125 immediately adjacent to the metallic plates 120, 121 and then to fill the gaps with some non-conductive material (which might even be a portion of the backing block 110 itself).

For well-known acoustic reasons, at least one matching layer is normally mounted on the upper, transmitting surface of the PZT element PZT element 115. FIG. 1 shows two matching layers: a first, high-impedance matching layer 140, and a relatively lower-impedance matching layer 142, on which is mounted the lens 144.

The high-impedance matching layer 140 is preferably made of graphite, aluminum, or any other acoustically suitable material that is also thermally conductive. This will then further heat transport to the side plates 120, 121, especially if these extend along the edges of at least the high-impedance matching layer 140. The bottom surface of the high-impedance matching layer 140 is preferably provided, for example by plating (sputtering) or attached foil, with a layer 145 of an electrically and thermally conductive material such as gold or nickel/copper. This layer 145 will not only conduct heat in the elevational direction away from the interior of the probe (the greatest area of thermal build-up will typically be in the center of the lens 144), towards the metallic plates 120, 121, but preferably also connects with the electrical ground formed by the plates 120, 121. Note that this reduces or eliminates the need for dedicated internal wires to provide a proper ground connection. Alternatively, if the high-impedance matching layer 140 itself is made of an electrically conductive material, then it could eliminate the need for the conductive layer 145 altogether while still providing the desired thermal and electrical conductivity.

Figure 3:
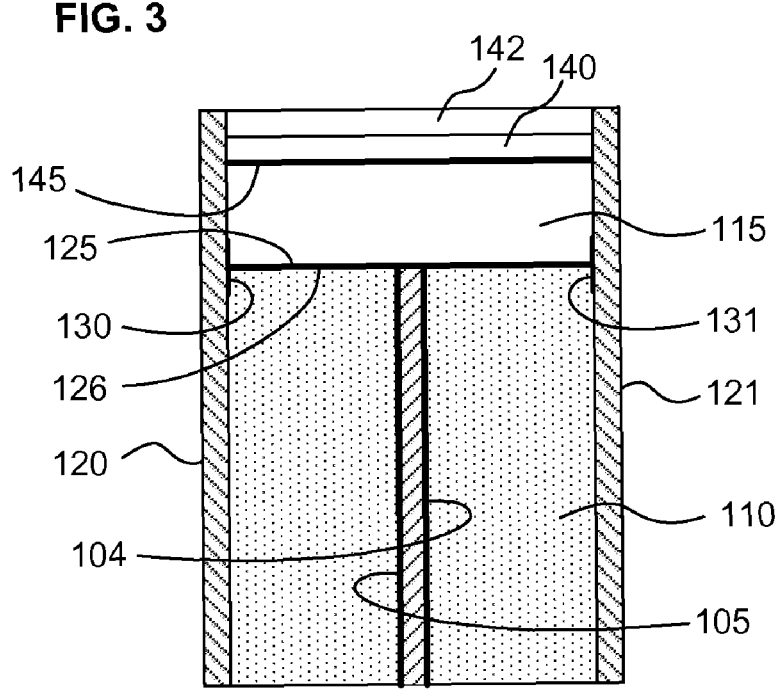
FIG. 3 shows a feature in which heat-conducting metallic members such as plates help lead heat away from not only an array of electro-acoustic elements, but also from at least one matching layer.

As FIG. 3 illustrates, the metallic plates 120, 121 could be allowed to extend along and be glued or otherwise attached to the outer edges of one or both (or all) of the matching layers 140, 141. The outer edge(s) of the matching layer(s) may then be plated to provide better heat transport to and electrical contact with the plate(s) 120, 121.

In many prior art transducers, the PZT elements and matching layer(s) are mounted in a recess in the top of the backing block. This at least partially traps heat in the recess. In embodiments such as the ones illustrated in the figures, any or all of the matching layer(s) 140, 141 may be made somewhat larger—as wide as or even wider than the top surface of the backing block, with one or even both being in direct thermal contact with the plates 120, 121. Together with the metallic plates 120, 121, this "oversized" matching layer structure may also add some protection for the PZT array in case the probe is dropped or otherwise subjected to some kind of impact: Some of the impact force will be transferred to the plates, which can then also transfer some of the force to the backing block backing block 110 or to other probe structures such as its housing, depending on the chosen design of the probe.

After the array 114 is laminated and diced (or the array is formed from individual PZT crystals), the plates 120, 121 are preferably added on the side of the array. The top edge of each plate 120, 121 is then preferably glued or otherwise attached to the high-impedance matching layer 140 using, for example, electrically conductive epoxy glue.

In common prior art arrangements, a single-sided, double-sided, or even multilayered flex circuit (also known as a flexible printed circuit or FPC) with deposited traces is used to carry electrical signals from the main system, and between (not within) the backing block 110 and the PZT element. In other words, the flex circuit is sandwiched between the PZT elements and the top of the backing block and extends laterally, in the elevation direction.

Such flex circuits, which are typically made of Kapton, along with their deposited traces, are usually more difficult to manufacture and are more fragile than standard PCB material. Moreover, being substantially rigid, a PCB is typically much more physically robust and does not require as complicated fabrication technology to work with successfully. Note that the preferred embodiment of one aspect of the invention does not need any flexible or otherwise non-rigid elements and provides one or even more thermal paths for heat to be removed from the PZT elements, the lens, etc. Furthermore, sandwiching a flex circuit between the backing block and the array also means that it is generally more difficult to provide a common electrical ground that is easily accessible by all internal parts of the probe.

A PCB generally enables easier, more reliable, and more consistent probe assembly—in assembling known ultrasound probes that use flex circuits, at least one array element is often made useless because of the bending of the flex circuit and breakage of the element's thin trace, and especially where the flex circuit has electrically conductive vias to connect traces. A suitable PCB may have traces up to about 20μ thick, that is, significantly thicker than what can usually be used reliably on a flex circuit, with no need for vias. A PCB is also usually much cheaper (on the order of about 4%) than a flex circuit. Furthermore, for high frequencies, a sandwiched flex circuit can influence the acoustic properties and performance of an ultrasound probe.

One concern about mounting a PCB within the backing block 102 might be that the backing block not be able to absorb all the generated sound it should, but rather that some sound would travel into the PCB 102 itself, would reflect, and would cause image noise. Experiments have shown, however, that this concern is generally unfounded. In one prototype of the invention, for example, the PCB 102 was 0.4 mm thick and was embedded in a backing block 11.6 mm thick. This provided attenuation great enough that no image was detectable on a standard oscilloscope; that is, the noise was at a negligible level. In general, the ratio of the PCB thickness to the block thickness should be low enough to avoid too much reflection. The proper thicknesses for any given application of the invention can be determined using known experimental design methods.

Figure 4:
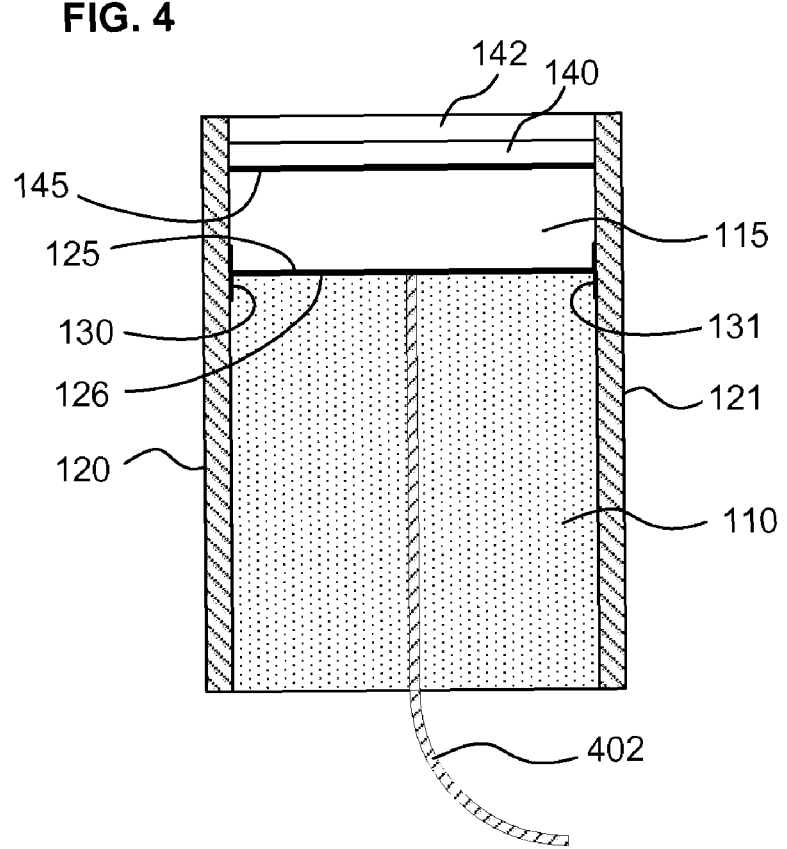
FIG. 4 shows a flex circuit used in place of a substantially rigid printed circuit board.

Nonetheless, as illustrated in FIG. 4, it would be possible to use a flexible material such as Kapton, that is, to use a flex circuit 402, in place of the more rigid PCB 102 as long as its drawbacks are taken into account and allowed for. (For clarity, in FIG. 4 the traces 104, 105 are not included.) The thinner profile of the flex circuit may be advantageous for some high-frequency probes, for example. One difficulty of this arrangement arises during the manufacturing process in that there typically must be some way to fix the flex circuit in the blocking frame as the blocking material is added and allowed to cure around the flex circuit. Any structure included within the backing block to accomplish this, however, may then itself interfere with acoustic integrity by internally reflecting or conducting sound energy, which could cause image noise. Even if one were to use a flex circuit as in FIG. 4, however, the other advantages of the invention, such as efficient thermal conduction and electrical grounding would still be available, however.

Note that the structure shown in FIG. 4, in which the flex circuit 402 is embedded within the backing block 110 and not just laid between the block and the PZT array, is physically more robust than the prior art arrangement and eliminates the PCB-to-PZT interface that the prior art must create during probe lamination. This not only reduces manufacturing cost, but also reduces the risk of breakage or faulty electrical contact. The structure shown in FIG. 4 avoids still other known problems of sandwiched structures such as the need for soldering to provide good contact between the flex circuit traces and the PZT elements. Because the flex circuit 402 in the illustrated embodiment does not enter from the side and does not lie between the backing block 110 and the PZT element PZT element 115, it is relatively easy to add the metallic plates 120, 121, which can provide both grounding and heat sinking.

FIG. 5 illustrates another embodiment of a transducer according to this invention. In FIG. 5, the structures identical or at least equivalent to those shown in FIG. 1 have the same reference numbers; the lens 144 has been removed for the sake of clarity. In this embodiment, however, instead of separate metallic plates 120, 121, a single "box," that is, enclosing member 520, which extends around the bottom and both sides of the backing block 110, but of course not obstructing the PZT elements in the longitudinal direction forward. This box should also be made of a thermally and electrically conductive metal such as aluminum, and could be fashioned by electroplating it onto the surfaces of the backing block 110, or by forming aluminum foil or a sheet around the block and bonding it, or by any other known method.

As before, the PZT elements (of which one element 115 is shown) of the array are mounted on the backing block 110, with the metallic layer 125 in between forming a substantially full-surface contact electrode. As with the embodiment shown in FIG. 1, the PCB 102 is fixed within and extends longitudinally through the backing block. In the embodiment of FIG. 5, the PZT element 115 does not extend laterally (in the elevational direction) all the way to the box 520. This is not required; rather, the width (as seen in FIG. 5) of the backing block relative to the array width can be chosen using known design considerations. If the backing block is wider than the PZT element 115, however, gaps 510, 512 will be formed on either side of the PZT element and the box. These gaps may be left unfilled; that is, they may be filled with air, which avoids creating a heat trap, or they could be filled with an electrically non-conductive but thermally well-conducting material to promote heat transfer to the box 520 without electrically shorting the PZT element 115 with other elements.

In FIG. 5, the matching layers 140, 141 are included as before, as well as the lens 144. In this embodiment, however, a layer 545—such as a sheet of foil—of an electrically and thermally conductive metal like copper is mounted between the innermost matching layer 140 and the upper surface of the PZT element 115. This layer 545 extends out to and is bonded (for example by simple soldering) to the member 520. In FIG. 5, the layer 545 is bonded to the upper edges of the member 520, which makes for easy manufacture; the layer could also be attached to the inside surface of the member 520 adjacent to the upper edges, however, as long as care is taken to prevent any electrical contact between the layer 545 and the layer 125. The layer 545 will then provide not only a thermal path to the member 520, but will also provide good electrical grounding to the common grounding structure that the member 520 provides.

FIGS. 6A-6F illustrate the main steps involved in manufacturing the probe shown in FIG. 1 and, with certain modifications that will be apparent to those skilled in the art, the other illustrated embodiments of the invention as well.

Figure 6A:
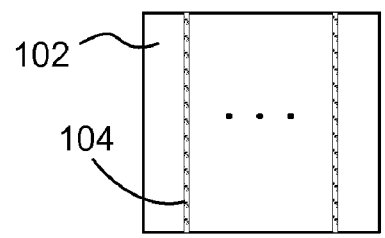
FIGS. 6A-6F illustrate various steps in a manufacturing process for one embodiment of the transducer.

FIG. 6A: Suitable PCB material is cut to size to form the PCB base 102. The traces 104 (and 105 on the back if needed) are then formed on the surface(s) of the PCB 102 in the normal manner. If the PCB 102 is to be multi-layer, then the traces will be formed using any known method.

Figure 6B:
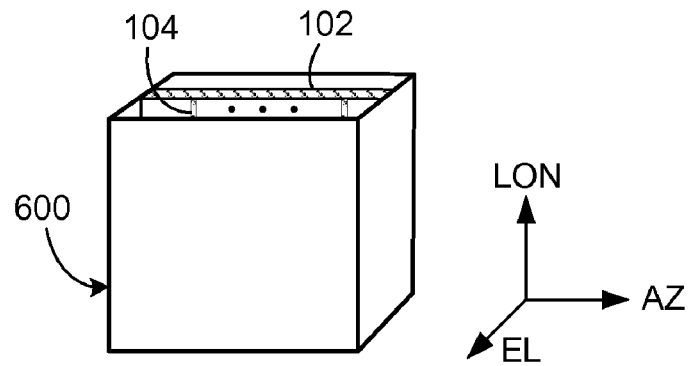

FIG. 6B: The PCB 102 is put in a conventional backing blocker 600. One advantage of using a PCB 102 is that it is relatively easy to fix it within the backing blocker, with no need for internal structures to keep it from flexing or warping or getting out of position, but that would remain within the cured backing block and potentially cause image noise.

Figure 6C:
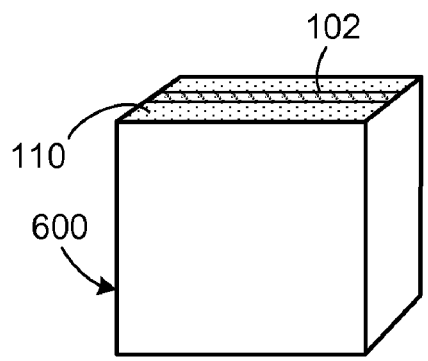

FIG. 6C: The chosen material for the backing block 110 is added, with the top edge of the PCB being flush with the top the backing block. If the lead wires 106 (not shown) are needed at all and have not already been joined with the traces, then this can be done before or after the PCB 102 has been put in the backing blocker. (The PCB could be allowed to extend from the bottom of the backing blocker during addition of the backing material.)

Figure 6D:
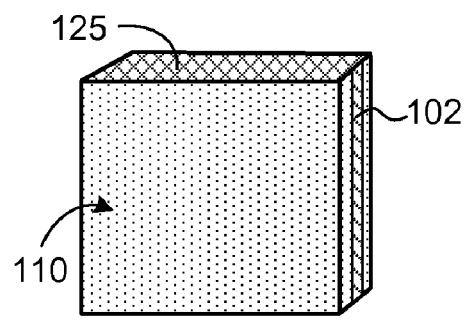

FIG. 6D: The conductive layer 125 is then sputtered or otherwise added onto the top of the block, which will also cause the sputtering material (such as copper) onto the top edge of the PCB. Note that by the very nature of the sputtering process onto the edge of the PCB 102, some of the sputtered metal will also contact the top portions of the traces 104, 105. In other words, as the inventor has confirmed through fabrication experiments, the sputtering process will not only form the top of the PZT electrode (the metallic layer 125), but will also establish an electrical path from each trace to its respective portion (after dicing) of the layer 125.

Figure 6E:
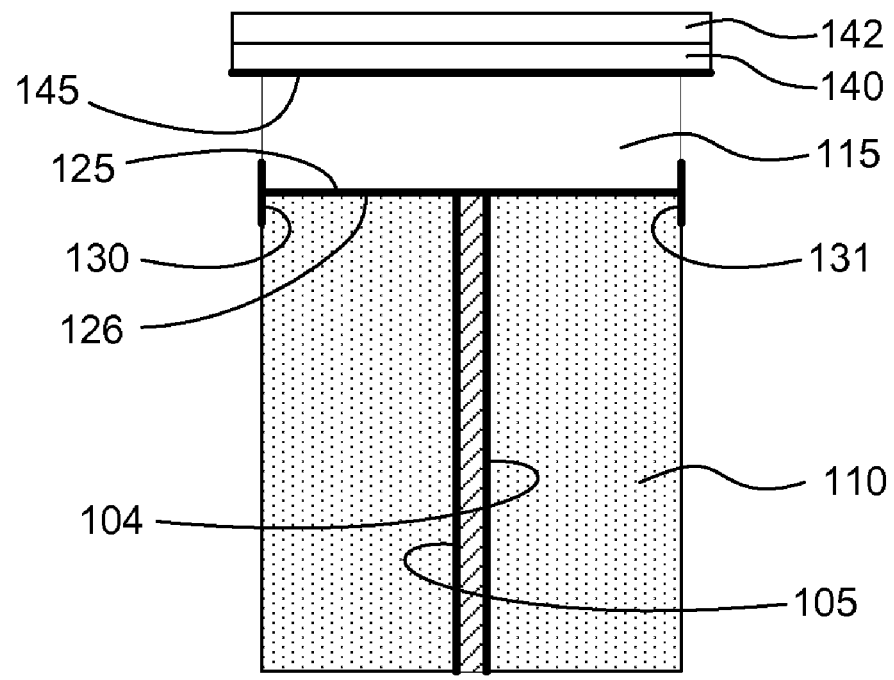

FIG. 6E (see also FIG. 2): After preparation, for example, addition of the conductive layers 126 and 145, the PZT material (or individual PZT crystals, if preferred) and matching layer(s) 140, 142 are then mounted on the backing block 110 using known methods. At this point, the array will essentially be a single large PZT element in contact with a single large electrode (the metallic layer 125). The PZT material and matching layer(s) are therefore separated by dicing into the backing block 110 to separate the PZT elements 115 both electrically and acoustically, such that one trace runs to a respective one of the PZT elements. Such dicing is common in transducer fabrication. Note that this dicing will also separate the metallic layer 125 into "strips," each corresponding to and in full bottom-surface contact with a respective one of the newly separated PZT elements 115. Heat will still flow outward (laterally, viewed as in FIG. 1) along each such strip, to the plates 120, 121. The plates 120, 121 themselves, however, do not need to be physically cut into pieces to prevent short-circuiting, since the easily installed insulating strips 130, 131 will prevent this.

Figure 6F:
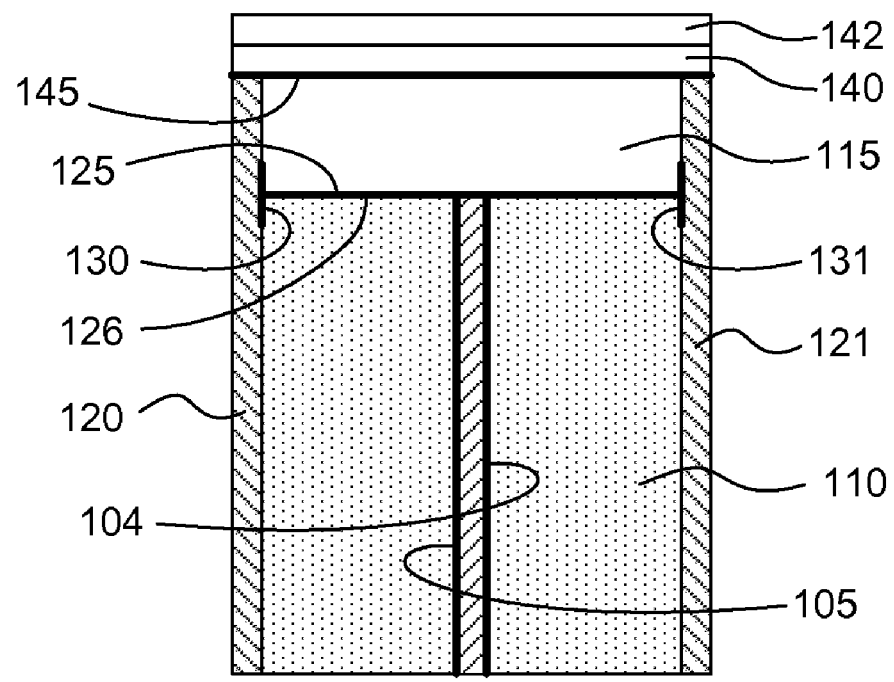

FIG. 6F: The insulating strips 130, 131 can then be attached along the intersection of the backing block 110 and the PZT array elements and the metallic plates 120, 121 can be mounted onto the backing block backing block 110. Alternatively, the enclosing member 520 can be electroplated or other formed on the backing block 110. The kerfs left from dicing can also be filled with any conventional material 214, which can be done at the same time the lens 144 is attached and may in fact be the same as the material that forms the lens.

What is claimed is:
1. An ultrasound imaging transducer comprising:
an array of electro-acoustic elements;
a backing block with a planar, non-recessed distal surface on which the array is mounted;
for each electro-acoustic element, an area of electrically conductive material on a corresponding portion of a contact surface of the backing block and in electrical contact with the electro-acoustic element;

a substantially rigid printed circuit board (PCB) secured to the backing block and extending in a longitudinal direction substantially perpendicular to the contact surface;

for each electro-acoustic element, at least one electrically conductive trace on the circuit board and in electrical contact with the corresponding contact surface portion and thereby with the electro-acoustic element, a solder-free electrical signal path thereby being formed through the trace to the electro-acoustic element metallic members mounted on opposing side surfaces of the backing block, each extending in a longitudinal direction at least as far distally as a distal surface of the electro-acoustic elements and forming a common electrical ground contact and a thermal path to an external heat sink.

2. The transducer of claim 1, in which the circuit board is embedded within the backing block.

3. The transducer of claim 1, in which the electrically conductive material is sputtered onto the contact surface of the backing block.

4. The transducer of claim 1, in which the PCB is mounted on a lateral surface of the backing block.

5. The transducer of claim 1, further comprising electrically insulating elements separating the metallic members from the electrically conductive material on the contact surface of the backing block.

6. The transducer of claim 1, wherein both metallic members are substantially perpendicular to the contact surface.

7. The transducer of claim 6, in which each metallic member is in physical contact with lateral surfaces of the electro-acoustic elements.

8. The transducer of claim 1, further comprising at least one acoustic matching layer mounted on a transmitting surface of the electro-acoustic element.

9. The transducer of claim 8, in which an edge region of each metallic member is in thermal contact with a respective edge portion of the matching layer.

10. The transducer of claim 9, further comprising a thermally conductive, metallic layer between the matching layer and the electro-acoustic element, the thermally conductive, metallic layer being in contact with the metallic members.

11. The transducer of claim 1, in which the electro-acoustic element is made of lead zirconate titanate (PZT).

12. The transducer of claim 1, further comprising an acoustic lens mounted longitudinally outward on the matching layer(s).

13. The transducer of claim 1, in which the metallic members are portions of a single metallic piece extending on either side of and across a proximal surface of the backing block.

* * * * *